Figure 1:
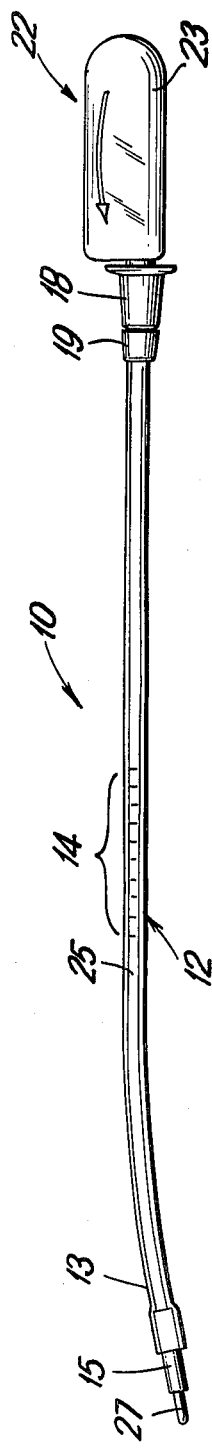

United States Patent [19]

Marx

[11] 4,396,022
[45] Aug. 2, 1983

[54] ENDOMETRIAL TISSUE SAMPLING APPARATUS

[76] Inventor: Alvin J. Marx, 107 Georgian Court Rd., Rochester, N.Y. 14610

[21] Appl. No.: 171,086

[22] Filed: Jul. 22, 1980

[51] Int. Cl.³ ............................................. A61B 10/00
[52] U.S. Cl. ..................................... 128/758; 128/304
[58] Field of Search ............... 128/758, 753, 754, 757, 128/304, 276

[56] References Cited

U.S. PATENT DOCUMENTS

| | | | |
|---|---|---|---|
| D. 210,757 | 4/1968 | Michel | 128/2 |
| 2,514,665 | 7/1950 | Myller | 128/2 |
| 2,516,492 | 7/1950 | Turkel | 128/2 |
| 2,955,591 | 10/1960 | MacLean | 128/2 |
| 3,394,699 | 7/1968 | Koett | 128/2 |
| 3,438,366 | 4/1969 | Kariher et al. | 128/2 |
| 3,527,203 | 9/1970 | Gravlee | 128/2 |
| 3,540,432 | 11/1970 | Ayre | 128/2 |
| 3,636,940 | 1/1972 | Gravlee | 128/2 |
| 3,727,602 | 4/1973 | Hyden et al. | 128/753 |
| 3,774,590 | 11/1973 | McDonald | 128/2 |
| 3,777,743 | 12/1973 | Benard et al. | 128/2 |
| 3,828,765 | 8/1974 | McDonald | 128/2 |
| 3,838,681 | 10/1974 | Dalton | 128/2 |
| 3,857,384 | 12/1974 | Watson | 128/2 |
| 3,945,372 | 3/1976 | Milan | 128/2 |
| 3,961,620 | 3/1973 | Schack et al. | 128/2 |

FOREIGN PATENT DOCUMENTS

| | | | |
|---|---|---|---|
| 270419 | 5/1965 | Australia | 128/2 |
| 214022 | 12/1968 | U.S.S.R. | 128/758 |

OTHER PUBLICATIONS

Endometrial Biopsy Curettes.

*Primary Examiner*—Kyle L. Howell
*Attorney, Agent, or Firm*—Stephen B. Judlowe

[57] ABSTRACT

Sampling apparatus for securing and removing endometrial tissue for pathological examination includes a thin elongated flexible sheath with a curved end portion terminating at an annular metallic tissue-scraping leading member. In use, the sheath with an inner path-dilating obturator is inserted into the endometrial cavity. The obturator is then removed, and a syringe attached to place the sheath under vacuum.

The composite apparatus is scraped across the endometrium to remove tissue samples which ultimately repose within the syringe for subsequent processing and analysis.

3 Claims, 2 Drawing Figures

U.S. Patent    Aug. 2, 1983    4,396,022

ENDOMETRIAL TISSUE SAMPLING APPARATUS

DISCLOSURE OF THE INVENTION

This invention relates to medical biopsy equipment and, more specifically, to an improved endometrial tissue curette assembly.

Despite modern early cancer detection devices, the death rate from carcinoma of the cervix is 10 per 100,000 per year with a disease incidence of 1,000 per 100,000 (Novak's Textbook of Gynecology, E. R. Novak et al., Waverly Press Ince., p. 246, 1975). The reported incidence of endometrial carcinomas varies from less than to nearly equal that of cervical carcinoma ("Gynecologic and Obstetric Pathology", E. R. Novak and J. D. Woodruff, W. B. Saunders Co., p. 204, 1979). The ratio of endometrial to cervical carcinoma has been rising over the last few decades ("The Changing Trends of Uterine Cancer and Cytology", Cancer, Vol. 42, pp. 2439–2449, November, 1979). This change in incidence may be a reflection of better treatment of cervical carcinoma and/or an aging population and/or the effect of exogenous estrogens.

However, fully satisfactory endometrial sampling apparatus for endometrical carcinoma screening and early detection - and for other purposes such as a fertility workup, has not heretofore been available. Available devices have been cumbersome, difficult to use, relatively expensive, and/or functionally imprecise in sometimes yielding endometrical cell sampling with cervical cells or sampling only exfoliated cells from the endometrium.

It is thus an object of the present invention to provide improved endometrial tissue/cell sampling apparatus which may be readily, safely, and reliably inserted, used, and removed to furnish its sample products; and which obtains sufficient intact individual and clumps of cells from the endometrium.

The above and other objects of the present invention are realized in specific, illustrative sampling apparatus for removing and securing endometrial tissue for pathological examination which includes a thin elongated flexible sheath with a curved end portion terminating in an annular metallic tissue-scraping leading member with a sharpened tip. In use, the sheath with an inner path-dilating pilot obturator is inserted into the endometrial cavity. The obturator is then removed, and a syringe attached to place the sheath under vacuum.

The composite apparatus is scraped across the endometrium to remove tissue samples which ultimately repose within the syringe for subsequent processing and analysis.

Figure 2:
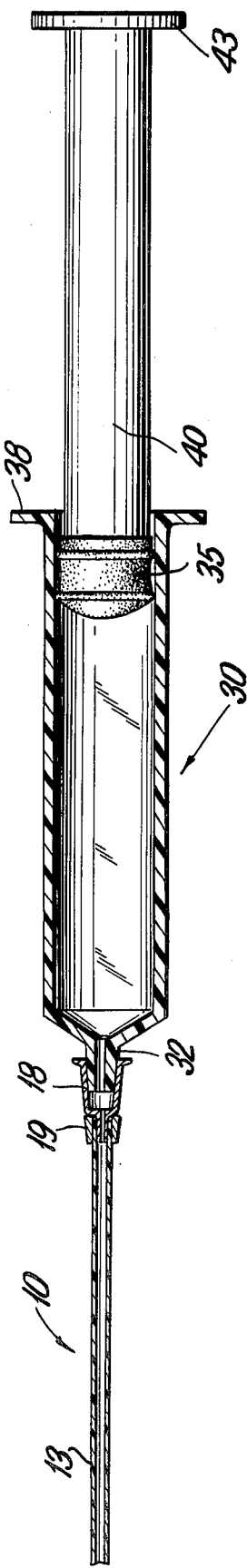

The above and other features and advantages of the present invention are realized in a specific, illustrative embodiment thereof, presented hereinbelow in conjunction with the accompanying drawing, in which:

FIG. 1 is an elevation view of an endometrial tissue curetting sheath 10 with an obturator 22 in place; and FIG. 2 depicts in cross-section the sheath 10 with a syringe 30 attached.

Referring now to the drawing and more particularly FIG. 1, there is shown a curetting sheath 10 (advantageously 2-4 mm and preferably 3 mm in outer diameter) having an elongated body portion 12, and a curved end portion 13 which surrounds and positively retains a hollow cylindrical thin wall metallic scraping tip 15. The body of the sheath is molded or otherwise marked with an insertion depth scale 14. The sheath other (right in FIG. 1) end terminates in a metallic receiver cylinder 18 with expanded head flange (inner taper) which is secured to the plastic sheath body 12 as by a compressed ferrule 19.

Initially concentrically reposing within the sheath 10 is an obturator 22 having an expanded end portion 23, an elongated body 25 radially within sheath body 12, and a rounded end 27 projecting through and axially beyond the metallic sheath cylinder 15. The sheath 10 and obturator 22 may be formed of plastic. Alternatively, one or the other may be formed of metal which can be bent to facilitate insertion into a markedly retroverted or anteverted uterus. The handle 23 designates the direction of curvature of sheath end portion 13 - as by a marked arrow as shown.

FIG. 2 depicts the sheath 10 with the obturator 22 removed, and a syringe 30 attached to the sheath via a projecting nipple 32 frictionally inserted in and retained by the metallic or plastic cylinder 18.

In use, the sheath 10 with the obturator 22 inserted (FIG. 1) is inserted with the guide/dilating elements 27-15 passing through the vagina, exocervix, squamocolumnar junction, endocervical canal and finally into the endometrial cavity. The scale 14 marks depth and the handle 23 signals orientation to facilitate insertion.

The obturator 22 is then removed, and the syringe 30 attached to sheath 10 with the syringe piston 35 fully inserted. The syringe actuator 40-43 is partially withdrawn (moved to the right in FIG. 2), thereby creating a vacuum within the sheath 10 (and within the endometrial cavity), binding the endometrium to the circular, exposed cutting edge of cylinder 15. The apparatus is then moved against the endometrium, removing tissue specimens which pass into the shaft and the body of the syringe.

When sufficient tissue has been dislodged, the plunger 40-43 is partially re-inserted to reduce the vacuum. The apparatus is then withdrawn.

The endometrial tissue collected by the instant apparatus is improved vis-a-vis prior art alternatives. The recovered tissue is largely undistorted. In taking the specimen the cervical tissue which does not enter the apparatus upon insertion or removal.

The endometrial tissue may be processed and analyzed by any manner per se well known to those skilled in the art. Thus, for example, if relatively large tissue samples have been removed, the syringe may draw in a fluid carrier (e.g., formalin or saline), and the sample-bearing carrier expelled into a container. The material may then be treated as a biopsy, by embedding the samples in paraffin after fixation, dehydration, cutting and staining to prepare the tissue for examination.

In accordance with a further aspect of the invention, if the recovered endometrial samples take the form of relatively small fragments, the carrier and samples are centrifuged to form a sample button (which is friable), and the supernate decanted. A protein-bearing fluid (e.g., plasma) is added to the sample button, and an acid (e.g., Carnoy's solution—a relatively weak acetic acid solution) added to precipitate the protein which forms a rubbery-like binding mass about the friable sample button. The plasma protein-bound sample may then be treated as a biopsy–for example, as described above.

The above-described arrangement and methodology is merely illustrative of the principles of the present invention. Numerous modifications and adaptations thereof will be readily apparent to those skilled in the art without departing from the spirit and scope of the present invention. Thus, for example, a prophylactic vaginal suppository could be administered in advance of the sheath/obturator to kill cervical bacteria, thus reducing the chance of endometrial infection.

What is claimed is:

1. In combination in endometrial tissue curretting apparatus, an elongated solid, unbroken wall sheath having an outer diameter in the range 2-4 mm, said sheath having a substantially straight major extent and a curved minor end extent to facilitate insertion through the exocervix, squamo-columar junction and endocervical canal into the endometrial cavity, a tissue scraping, sharpened circumferential end-sampling metallic cylinder retained by and projecting from said sheath minor end portion, path dilating obturator means adapted to reside within said sheath and being longer than said sheath to extend therefrom when reposing within said sheath upon insertion to obviate spurious tissue sampling upon insertion, said sheath having first connection means at the end thereof opposite said minor end extent, and syringe means including second connection means adapted for communicating engagement with said first connection means of said sheath.

2. A combination as in claim 1 wherein said first connection means comprises cylindrical means and ferrule means for securing said cylindrical means to said sheath, and wherein said syringe includes projecting means for engaging said cylindrical means.

3. A combination as in claim 1 or 2 further comprising means secured to said sheath and having a predetermined fixed alignment relationship with said sheath curved minor end extent for signalling the then-obtaining orientation of said curved sheath end extent.

* * * * *